US007027870B2

(12) United States Patent
Limousin et al.

(10) Patent No.: US 7,027,870 B2
(45) Date of Patent: Apr. 11, 2006

(54) MANAGING DATA FOR CLINICAL PROTOCOLS RELATING TO THE USE OF ACTIVE IMPLANTABLE MEDICAL DEVICES

(75) Inventors: Marcel Limousin, Paris (FR); Remi Nitzsche, Bourdonne (FR)

(73) Assignee: ELA Medical S.A., Montrouge (FR)

( * ) Notice: Subject to any disclaimer, the term of this patent is extended or adjusted under 35 U.S.C. 154(b) by 496 days.

(21) Appl. No.: 10/132,057

(22) Filed: Apr. 23, 2002

(65) Prior Publication Data
US 2002/0169488 A1 Nov. 14, 2002

(30) Foreign Application Priority Data
Apr. 23, 2001 (FR) ................................. 01 05439

(51) Int. Cl.
*A61N 1/00* (2006.01)
(52) U.S. Cl. ....................................................... 607/59
(58) Field of Classification Search ................. 607/59, 607/31

See application file for complete search history.

(56) References Cited

U.S. PATENT DOCUMENTS

| 5,660,183 | A | | 8/1997 | Chiang et al. | |
|---|---|---|---|---|---|
| 5,693,076 | A | | 12/1997 | Kaemmerer | |
| 5,722,999 | A | * | 3/1998 | Snell | 607/32 |
| 5,724,985 | A | | 3/1998 | Snell et al. | |
| 6,480,745 | B1 | * | 11/2002 | Nelson et al. | 607/60 |
| 6,687,190 | B1 | * | 2/2004 | Momich et al. | 368/10 |

FOREIGN PATENT DOCUMENTS

| EP | 0 761 255 A1 | 3/1997 |
|---|---|---|
| WO | WO 93/08872 | 5/1993 |

* cited by examiner

*Primary Examiner*—Scott M. Getzow
(74) *Attorney, Agent, or Firm*—Orrick Herrington & Sutcliffe LLP

(57) ABSTRACT

A process for managing data collection for clinical protocols and investigations (registry) relating to the use of active implantable medical devices, such as pacemaker, cardiovertor, defibrillator and multisite devices. This process is characterized by the following stages:
1) preliminarily initializing a plurality of implants, by writing, in a protocol identification zone provided in a memory of the implant, a protocol identification code common to all the aforementioned implants taking part in the given clinical protocol, and
2) at each interrogation of any implant by a practitioner by use of a compatible programmer:
  a) searching for a protocol identification zone in the memory of the implant and reading the contents thereof,
  b) determining the presence of a protocol identification code in that zone,
  c) in the event of presence of a protocol identification code:
    c1) recognizing the protocol identification code by the programmer,
    c2) displaying on a screen of the programmer an appropriate questionnaire for the protocol identified by the aforementioned code,
    c3) capturing answers to that the questionnaire input by a practitioner using the programmer, and
    c4) memorizing these answers in a memory of the programmer.

14 Claims, No Drawings

MANAGING DATA FOR CLINICAL PROTOCOLS RELATING TO THE USE OF ACTIVE IMPLANTABLE MEDICAL DEVICES

FIELD OF THE INVENTION

The present invention is directed to "active implantable medical devices" as such devices are defined by the Jun. 20, 1990 directive 90/385/CEE of the Council of the European Communities. This definition includes pacemaker, defibrillator, cardiovertor and/or multisite devices for the treatment of the disorders of the cardiac rhythm, and neurological apparatuses, medical substance diffusion pumps, cochlear implants, implanted biological sensors, etc., as well as devices for the measurement of pH or an intra-corporeal impedance (such as the measurement of the transpulmonary impedance or the intracardiac impedance). These devices, simply called herein after "implants," comprise a data memory which can be read by means of an external programmer by telemetry techniques in themselves well-known to persons of ordinary skill in the art. The programmer is associated with a microcomputer at the disposal of the practitioner, comprising a display screen, a keyboard or other input interface for the entry of control commands and data, as well memory and associated software for data memorizing (storage) and data processing.

BACKGROUND OF THE INVENTION

Implants, and in particular those that have been recently developed, can be the subject of procedures called "clinical trials" and/or "clinical protocols", according to which, among a population of patients carrying a model of a given implant, certain of these patients are selected to be the subject of a more specific follow-up. This follow-up generally involves complementary examinations, consultations, and care. The results of the follow-up examinations are collected and compiled for statistical study of the selected population of patients.

The present invention concerns a process for managing the data acquired in connection with such clinical trials and protocols, in particular allowing for a more regular and exhaustive follow-up and avoiding, by dematerialization of the collected information, the recourse to paper questionnaires or follow-up cards that heretofore have been filled out by hand by the practitioner when he or she examines one of the patients selected for the clinical study or concerned with clinical protocol.

The invention also applies, mutatis-mutandis, to the management of the data for a "registry" or a "investigation", i.e. a procedure implying (as compared with a clinical protocol) monitoring all of the patients in the population carrying an implant of a given model. The data concerned here are data simply collected, in particular in the aim of epidemiological studies, at the time of the interrogations of the implant, whether routine interrogations or interrogations following an evolution of the pathology of the patient, but without either a particular examination or more constraining follow-up procedures as occur in the case of clinical protocols.

OBJECTS AND SUMMARY OF THE INVENTION

The present invention broadly proposes an improved process for the management of data collected during interrogation of an implant. Once aspect of the invention is directed towards a process for the improved management of the data of clinical protocol, characterized by the following stages:

1) preliminarily initializing a plurality of like implants taking part in a given protocol by writing of a protocol identification code in a protocol identification zone provided in a memory of the implant, and
2) at each interrogation of any implant by a programmer:
   a) searching for a protocol identification zone within the memory of said implant and reading the contents of said protocol identification zone,
   b) determining a presence of a protocol identification code in said contents, and
   c) in the event of a determined protocol identification code:
      c1) recognizing the protocol identification code,
      c2) displaying on a screen of the programmer an appropriate questionnaire for the protocol identified by the aforementioned protocol identification code,
      c3) inputting answers to said displayed questionnaire using the programmer, and
      c4) memorizing said input answers in a memory of the programmer.

Another aspect of the present invention is directed to a process for the management of a data registry, characterized by the following stages, carried out at each interrogation of an implant by an practitioner using a programmer:

a) reading in a memory of the implant the contents of an identification zone of the model of implant,
b) recognizing the implant model from said contents read by the programmer,
c) displaying on a screen of the programmer, a specific questionnaire for said model of implant,
d) inputting answers to said questionnaire using the programmer; and
e) memorizing the input answers in a memory of the programmer.

In either of the aforementioned aspects of the invention, it is possible to envisage various particularly advantageous embodiments, including additional steps of using the programmer to read the setting parameter data and/or the Holter data contained in a memory of the implant, and storing such data in the memory of the programmer jointly with the answers to the questionnaire.

Another embodiment includes a step, carried out periodically, of the collection and/or centralization (hereinafter generally referred to as "aggregation") for treatment at a later date of the answers, and, as the case might be, the setting parameter data and/or the Holter data, relating to a plurality of implants, and memorizing the aggregated data in a given programmer or in a plurality of programmers.

In yet another embodiment, the method may include a stage of presentation to the practitioner, by displaying on the screen of the programmer, a reminder message to carry out a complementary examination and/or an informative message about the next stage of the patient follow-up.

Still another embodiment concerns reading in the memory of the implant the implantation date and/or the date of the last interrogation of the implant, such that the presentation of the questionnaire is conditioned based upon at least one of these dates. In other words, based on the date stored and the date of the follow up, a particular questionnaire will be automatically presented or not, as is appropriate for the given situation.

In addition, the questionnaire and its answers can be memorized in the memory of the implant and be read therein in order to be presented to the practitioner on the screen of the programmer.

DETAILED DESCRIPTION OF THE INVENTION

Other features, characteristics, and advantages of the present invention will appear to a person of ordinary skill in the art in view of the following detailed description of preferred embodiments of the present invention.

The present invention starts from the inventors' observation that it is always difficult for an practitioner (a clinical investigator or doctor) to take part correctly in a clinical protocol or a "registry." Essentially, any follow-up for a patient implanted with a device begins with an interrogation by a programmer. The invention proposes to integrate into this programmer the capture of the questionnaires from a clinical protocol or registry. More precisely, the management of the questionnaire of a clinical protocol or a registry is operated at the end of the examination, after the practitioner has carried out the traditional operations of a follow-up examination or consultation, as the case may be. Thus, for example, at the moment when the practitioner exits the follow-up program, the programmer displays a reminder message that the implant takes part in a clinical protocol or an investigation (registry). The programmer searches at the beginning of the interrogation for specific information in the implant memory allowing it to recognize this participation.

In the case of a clinical protocol, it is thus possible to provide in the memory of a pulse generator a protocol identification zone where the code name identifying the protocol will have been registered beforehand, for example, after the patient signed his or her consent to take part in the study. In the case of a registry, it is possible for the programmer to determine the model identification number by an interrogation of the implant to determine if the implant model is or is not concerned with a registry.

An additional criterion to decide whether or not it is necessary to present a questionnaire to the doctor can be derived from the date of implantation of the device and/or a delay period for follow-up, calculated starting from the current date back to the date of the last examination, memorized in the implant. The programmer thus determines whether the implant takes part in a clinical protocol or a registry. In the affirmative, the questionnaire display is conditioned upon the stored date such that the programmer then proposes an appropriate questionnaire to the practitioner by a special display on a screen. In response, the practitioner keyboards or otherwise inputs the requested data through an interface (e.g., mouse clicks, light pen, touch screen, voice activated software, etc.), if necessary after having carried out complementary examinations (in the case of a clinical protocol). The answers to the questionnaire are then memorized by the programmer preferably in a database contained in it. Preferably also at the same time the programmer memorizes the interrogation files, i.e., the files containing the setting parameter data and/or the Holter data read from the memory of the implant. Once the questionnaire is thus captured and the input answers memorized, the programmer can propose to the practitioner to carry out a complete interrogation of the implant memories if that were not already done, and/or to remind the practitioner to carry out some other examination within the framework of the protocol (effort test, echocardiography, etc.) and/or to indicate the next stage of the protocol (for example "to re-examine the patient in six months"), or indicate the date by which the next routine examination is to be carried out. The data thus collected and memorized in the programmer then can be aggregated regularly, e.g., by diskette or tele-transmission, in a common database for statistical processing, safeguard of the registry for the complete set of the examined apparatuses, etc.

Very advantageously, the contents of the questionnaire (the formulation of the questions) are preserved in the memory of the implant, thus rendering the procedure of the invention completely independent of the programmer used, regardless of whether the programmer is dedicated to the implant or is up to date. This manner of proceeding according to the invention present one or more of the following advantages:

First, it makes it possible to have an at the same time a complete and ordered questionnaire: It also makes it possible to be freed from the need for transcription on paper, thus eliminating the risks of error and avoiding the recourse, as exists in the art today, to a double capture of the handwritten forms (capture+checking). In addition, it avoids any risk that the doctor does not remember that his patient takes part in a clinical study, because the questionnaire is systematically and automatically presented to the practitioner at the end of the examination, if (and only if) the patient takes part in the clinical protocol. Further, the questionnaire, in particular if it is memorized in the implant, is immediately placed at the disposal of the practitioner, in an entirely dematerialized way without it being necessary to use a paper file.

It also should be noted that the questionnaire displayed need not be the same each time, such that under different conditions or at different times, the practitioner may collect more or different information for storage.

It should be understood that the present invention is preferably implemented in software of a microprocessor controlled implantable medical device and its cooperating programmer device. Suitable implantable devices include, but are not limited to commercial pacemaker products sold under the Talent™ brand, available from Ela Médical, Montrouge, France. Advantageously, the present invention can be downloaded to an already implanted device by its external programmer, in a conventional manner, as software instructions to modify the operation of the already implanted device, for such devices that are able to receive software instructions and to modify its operation in response thereto.

One skilled in the art will appreciate that the present invention can be practiced by other than the described embodiments, which are presented for purposes of illustration and not of limitation. Indeed, the time periods and other values discussed are merely preferred parameters as a design choice and not limiting on the scope of the invention.

We claim:

1. A process for managing data collection for clinical protocols having as a subject the use of an implant of an active implantable medical device type, such as a pacemaker, a defibrillator, a cardiovertor and/or a multisite device, comprising:

a) initializing preliminarily a plurality of implants taking part in a clinical protocol and having a protocol identification zone by writing a protocol identification code in said protocol identification zone common to said plurality of implants;

b) providing a programmer having a memory and a display screen, said programmer being able to interrogate at least one of said implants;

c) interrogating an implant using said programmer and, at each interrogation:
   i) searching for a protocol identification zone in said memory of the implant and reading the contents thereof,
   ii) determining a presence of a protocol identification code in said protocol identification zone contents, and
   iii) in the event of a detected protocol identification code:
      recognizing the protocol identification code using the programmer,
      displaying on said programmer screen a questionnaire associated with the identified protocol identification code,
      capturing answers to that questionnaire using the programmer, and
      memorizing said answers in said programmer memory.

2. The process of claim 1, further comprising, in the event of a presence of a protocol identification code, the steps of:
   reading, using the programmer, one of a parameter setting data and a Holter data contained in the implant memory, and
   memorizing said read data in the memory of the programmer jointly with the captured answers to the questionnaire.

3. The process of claim 1, further comprising, in the event of a presence of a protocol identification code, displaying on the programmer screen a text message representative of one of a reminder message of a complementary examination to carry out and an informative message about a next stage of protocol.

4. The process of claim 1, wherein stage a) further comprises reading in the implant memory a date corresponding to one of an implantation date and a date of the last interrogation of the implant, wherein displaying the questionnaire is conditioned by said date.

5. The process of claim 1, further comprising memorizing said questionnaire in the implant memory, and wherein stage c) further comprises reading said questionnaire in said implant memory and displaying said questionnaire.

6. A process for managing a registry data on the use of active implantable medical device implants, such as a pacemaker, a defibrillator, a cardiovertor and/or a multisite device, comprising:
   a) providing an implant taking part in a registry and having a memory, said memory having an identification zone containing a content;
   b) providing a programmer having a telemetry function for reading said implant memory, a display screen for displaying information, and a memory, said memory containing a questionnaire associated with an implant identification content;
   c) successively interrogating an implant using said programmer, and on each interrogation of an implant:
      i) reading in the implant memory the contents of the identification zone of the implant model,
      ii) recognizing of the implant model in response to the read identification zone contents,
      iii) displaying on the programmer screen said questionnaire associated with said recognized implant model,
      iv) inputting answers to that said questionnaire using said programmer, and
      v) memorizing said answers in the programmer memory.

7. The process of claim 6, wherein said implant memory further comprises one of parameter setting data and Holter data and the process further comprises:
   d) reading, using the programmer, said one of the parameter setting data and the Holter data contained in the implant memory, and
   e) memorizing in the programmer memory said read data jointly with the answers to the questionnaire.

8. The process of claim 6, further comprising, in response to a recognized implant model code, displaying on the programmer screen one of a reminder message to carry out a complementary examination and an informative message about a next interrogation of the implant.

9. The process of claim 6, wherein stage a) further comprises reading in the implant memory one of an implantation date and a date of the last interrogation of said implant, wherein displaying the questionnaire at stage c) is conditioned by said at least one read date.

10. The process of claim 6, further comprising storing said questionnaire in the implant memory wherein stage c) further comprises reading in said implant memory the questionnaire to be displayed.

11. A process for managing data collection for clinical protocols having as a subject the use of an implant of an active implantable medical device type, such as a pacemaker, a defibrillator, a cardiovertor and/or a multisite device, comprising:
   a) initializing preliminary a plurality of implants having a protocol identification zone by writing a protocol identification code in said protocol identification zone common to said plurality of implants taking part in said protocol;
   b) providing a programmer having a memory and a display screen, said programmer being able to interrogate at least one of said implants;
   c) interrogating an implant using said programmer and, at each interrogation:
      i) searching for a protocol identification zone in said memory of the implant and reading the contents thereof,
      ii) determining a presence of a protocol identification code in said protocol identification zone contents, and
      iii) in the event of a detected protocol identification code:
         recognizing the protocol identification code using the programmer,
         displaying on said programmer screen a questionnaire associated with the identified protocol identification code,
         capturing answers to that questionnaire using the programmer,
         memorizing said answers in said programmer memory,
         reading, using the programmer, one of a parameter setting data and a Holter data contained in the implant memory,
         memorizing said read data in the memory of the programmer jointly with the captured answers to the questionnaire,
         periodically aggregating for a secondary processing the answers and said one of the parameter setting data and the Holter data for said plurality of implants taking part in said protocol, and
         memorizing said periodically aggregated data in one of a programmer and a plurality of programmers.

12. A process for managing data collection for clinical protocols having as a subject the use of an implant of an active implantable medical device type, such as a pacemaker, a defibrillator, a cardiovertor and/or a multisite device, comprising:
- a) initializing preliminary a plurality of implants having a protocol identification zone by writing a protocol identification code in said protocol identification zone common to said plurality of implants taking part in said protocol;
- b) providing a programmer having a memory and a display screen, said programmer being able to interrogate at least one of said implants;
- c) interrogating an implant using said programmer and, at each interrogation:
  - i) searching for a protocol identification zone in said memory of the implant and reading the contents thereof,
  - ii) determining a presence of a protocol identification code in said protocol identification zone contents, and
  - iii) in the event of a detected protocol identification code:
    - recognizing the protocol identification code using the programmer,
    - displaying on said programmer screen a questionnaire associated with the identified protocol identification code,
    - capturing answers to that questionnaire using the programmer,
    - memorizing said answers in said programmer memory,
    - periodically aggregating for a secondary processing the answers for said plurality of implants taking part in said protocol; and
    - memorizing said periodically aggregated data in one of a programmer and a plurality of programmers.

13. A process for managing a registry data on the use of active implantable medical device implants, such as a pacemaker, a defibrillator, a cardiovertor and/or a multisite device, comprising:
- a) providing an implant having a memory, said memory having an identification zone containing a content, and further comprising one of parameter setting data and Holter data;
- b) providing a programmer having a telemetry function for reading said implant memory, a display screen for displaying information, and a memory, said memory containing a questionnaire associated with an implant identification content;
- c) successively interrogating an implant using said programmer, and on each interrogation of an implant:
  - i) reading in the implant memory the contents of the identification zone of the implant model,
  - ii) recognizing of the implant model in response to the read identification zone contents,
  - iii) displaying on the programmer screen said questionnaire associated with said recognized implant model,
  - iv) inputting answers to that said questionnaire using said programmer,
  - v) memorizing said answers in the programmer memory,
  - vi) reading, using the programmer, said one of the parameter setting data and the Holter data contained in the implant memory,
- e) memorizing in the programmer memory said read data jointly with the answers to the questionnaire, and
- f) periodically aggregating said questionnaire answers and said read data for a plurality of implants memorized in a programmer or a plurality of programmers for secondary treatment.

14. A process for managing a registry data on the use of active implantable medical device implants, such as a pacemaker, a defibrillator, a cardiovertor and/or a multisite device, comprising:
- a) providing an implant having a memory, said memory having an identification zone containing a content;
- b) providing a programmer having a telemetry function for reading said implant memory, a display screen for displaying information, and a memory, said memory containing a questionnaire associated with an implant identification content;
- c) successively interrogating an implant using said programmer, and on each interrogation of an implant:
  - i) reading in the implant memory the contents of the identification zone of the implant model,
  - ii) recognizing of the implant model in response to the read identification zone contents,
  - iii) displaying on the programmer screen said questionnaire associated with said recognized implant model,
  - iv) inputting answers to that said questionnaire using said programmer,
  - v) memorizing said answers in the programmer memory;
  - vi) periodically aggregating said questionnaire answers relating to a plurality of implants memorized in a programmer or a plurality of programmers for secondary treatment.

* * * * *